US006702756B2

(12) United States Patent
Brown

(10) Patent No.: US 6,702,756 B2
(45) Date of Patent: Mar. 9, 2004

(54) METHOD AND APPARATUS FOR DIAGNOSING NEUROLOGICAL IMPAIRMENT

(75) Inventor: Lenora Brown, Calgary (CA)

(73) Assignee: University Technologies International Inc., Calgary (CA)

( * ) Notice: Subject to any disclaimer, the term of this patent is extended or adjusted under 35 U.S.C. 154(b) by 0 days.

(21) Appl. No.: 09/683,302

(22) Filed: Dec. 11, 2001

(65) Prior Publication Data

US 2003/0109799 A1 Jun. 12, 2003

(51) Int. Cl.$^7$ ............................................. A61B 19/00
(52) U.S. Cl. ........................ 600/558; 600/557; 600/300
(58) Field of Search ................................. 600/300, 544, 600/552–554, 557, 558; 128/897, 898

(56) References Cited

U.S. PATENT DOCUMENTS

| 5,363,859 A | * | 11/1994 | Tuckett et al. | ............... 600/552 |
| 5,746,205 A | * | 5/1998 | Virsu et al. | ................. 600/544 |
| 6,409,655 B1 | * | 6/2002 | Wilson et al. | ................ 600/28 |
| 6,422,869 B1 | * | 7/2002 | Nagarajan et al. | .......... 434/156 |

OTHER PUBLICATIONS

Brown, Lenora N; "Hemispheric Equivalence in the Temporal Processing for Somatosensory and Visual Stimuli: Age–Related Differences" Universary of Calgary (Canada) vol. 59/12–B of Dissertation Abstracts International; 1998, p. 6483.*

Davidson et al.; "Reaction Time Measures of Interhemispheric Transfer Time in Reading Disabled and Normal Children" Neuropsychologia; vol. 28, Issue 5, 1990, pp. 471–485 (Abstract only).*

Brown, Lenora and Sainsbury, Robert; "Hemispheric Equivalence and Age–Related Differences in Judgments of Simultaneity to Somatsosensory Stimuli" Journal of Clinical and Experimental Neuropsychology 2000, vol. 22, No. 5, pp. 587–598, Oct. 2000.

* cited by examiner

Primary Examiner—Charles Marmor
(74) Attorney, Agent, or Firm—Bennett Jones LLP

(57) ABSTRACT

A method of diagnosing neurological impairments such as multiple sclerosis includes the determination of the simultaneity threshold of a pair of sensory stimuli, such as visual or tactile stimuli, separated temporally by a stimulus onset asynchrony (SOA). The stimuli may be presented unilaterally or bilaterally. Interhemispheric transfer times may also be determined by determining the difference in simultaneity thresholds for bilateral and unilateral presentations. Simultaneity thresholds and interhemispheric transfer times are significantly elevated in patients with MS and other neurological impairments. An apparatus for delivering such sensory stimuli includes an array of visual stimuli and tactile stimulators, a computer-implemented control program and a precise timing mechanism.

18 Claims, 3 Drawing Sheets

METHOD AND APPARATUS FOR DIAGNOSING NEUROLOGICAL IMPAIRMENT

BACKGROUND OF THE INVENTION

The present invention relates to methods and apparatuses for diagnosing or monitoring neurological impairments such as multiple sclerosis.

Slowing of the nervous system occurs as a consequence of both normal aging and neurological impairment. It is well documented that older individuals require a longer period of time to process information relative to younger individuals. It is generally believed that the slowing in the nervous system was mainly related to decision time and motor response because much of the research had focused on motor output (i.e., reaction time) relative to sensory input. However, sensory input and global higher order brain processing may also be significantly affected by neurological impairment, both as a result of injury or disease, or as a result of normal aging.

Multiple sclerosis (MS) is a disease involving neurological impairment which often begins with a history of fluctuating, hard to describe, and seemingly minor, symptoms that family and friends dismiss or discount. These symptoms often resolve without treatment, but continue to return. The initial symptoms of MS are most often: difficulty in walking; abnormal sensations such as numbness or "pins and needles"; and pain and loss of vision due to optic neuritis, an inflammation of the optic nerve. Less common initial symptoms may include: tremor; incoordination; slurred speech; sudden onset of paralysis similar to a stroke; and a decline in cognitive function.

These symptoms are a direct result of demyelination, the destruction of myelin—the fatty sheath that surrounds and insulates nerve fibers in the central nervous system, as well as axonal injury and neuronal death. This impairs transmission of nerve impulses to muscles and other organs.

When doctors suspect multiple sclerosis, they thoroughly evaluate the nervous system as part of the physical examination. Signs that the nervous system isn't functioning properly, such as uncoordinated eye movements, muscle weakness, or numbness in scattered parts of the body; other findings such as inflammation of the optic nerve; and symptoms that wax and wane make the diagnosis fairly certain.

Diagnostic imaging using magnetic resonance imaging (MRI) is a sensitive technique, possibly revealing areas of the brain that have lost myelin. An MRI scan may even distinguish areas of active, recent demyelination from areas in which demyelination took place some time ago. In an evoked potentials test, electrical responses in the brain are recorded when nerves are stimulated. For example, normally the brain responds to a flash of light or a noise with characteristic patterns of electrical activity; in people with multiple sclerosis, the response may be slower because signal conduction along demyelinated nerve fibers is impaired.

One of the problems in assessing a patient with neurological impairment is that the tests often are expensive (e.g., MRI), time-consuming, and/or invasive. In respect of MS, there is no single measure or test that reliably detects pathologic change. The most common clinical test used to measure disease burden of MS is the extended disability status scale (EDSS) which primarily measures motor output, but it is insensitive to change. Evoked potentials evaluate nerve conduction in some central pathways, but have not proven to be a sensitive measure of disease progression. MRI is useful, but it monitors or detects anatomical changes that follow nerve injury (atrophy and black holes). Moreover, white matter has appeared normal on MRI, yet it is often abnormal when assessed by magnetic resonance spectroscopy (MRS). MRS assesses brain metabolism which is an indication of nerve 'health' not nerve dysfunction. Since physiologic changes precede irreversible anatomic changes, a tool that assesses physiological function would be valuable in neurological assessment and disease burden.

Sensory symptoms such as numbness, "pins and needles", pain, loss or interruption of vision (e.g., optic neuritis) tend to precede symptoms of motor dysfunction. Unfortunately, neurological diagnostic/monitoring tests tend to measure motor output (e.g., EDSS) as opposed to measuring the function of sensory pathways. Therefore, tests which measure impairment of sensory pathways, or global higher order brain processing, may detect neurological impairment earlier and more reliably than those tests which measure motor output.

Furthermore, since myelin injury causes reduced nerve conduction, central conduction times may be considered as a useful outcome measure. More specifically, lesions to the pathway connecting the two hemispheres, the corpus callosum, is well noted in the multiple sclerosis literature. Given that interhemispheric transfer times (IHTTs) represent global higher order brain processing, the integration of information between and within hemispheres, deterioration of IHTTs may be an indicator of cognitive dysfunction. There is a need in the art for tests that may measure IHTT as part of a clinical battery for neurological impairment.

SUMMARY OF THE INVENTION

The present invention is directed to methods and apparatuses for the diagnosis or monitoring, or both, of neurological impairments by providing an objective measurement of neural function that is relatively inexpensive, easy and quick to administer, and noninvasive. It is an objective technique that also has demonstrable sensitivity to central nerve conduction. The technique may employ a lateralized perspective such that neural function within and between cerebral hemispheres is measured. The lateralized perspective also allows assessment to one side of the body, which is important since many patients and doctors report that symptoms are sometimes lateralized to one side of the body, or to half a visual field.

The present invention was devised to measure sensory functioning of the nervous system without confounding reaction time which includes decision time and motor response time. The invention was also devised so that an estimate of interhemispheric transfer time (IHTT) between cerebral hemispheres could be calculated. High IHTTs would indicate that there is a slowing of central, higher order neural processing as opposed to peripheral neural processing which is typically measured in reaction time tasks. The methods of the present invention demonstrate a sensitivity to both a neurological sensory impairment and interhemispheric transfer dysfunction in patients exhibiting a neurological impairment and therefore may be used in the diagnosis and monitoring of such impairments in patients.

The applicants have found that threshold of simultaneity, which is the minimum temporal separation of two stimuli presented to a patient necessary for a patient to perceive the two stimuli as sequential rather than simultaneous, is greatly increased in patients who suffer from a neurological impairment. Pairs of stimuli are delivered in bilateral or unilateral situations. Interhemispheric transfer is required with bilateral stimulation since each hemisphere receives information regarding the stimulus that was presented to the opposite visual field or to opposite side of the body. That is, since a comparison has to be made regarding the onset of each stimulus, the information needs to be integrated from each hemisphere. The point at which a person perceives the onset of two stimuli as occurring simultaneously is the simultaneity threshold. Thus, the simultaneity threshold is the smallest interval that separates the onset of two stimuli which is perceived by the patient as a separation. The applicants have found that simultaneity thresholds and IHTTs are significantly greater in patients who suffer neurological impairment.

The applicants have further found that the threshold of simultaneity can be quantified and measured against the patient's own baseline data, and data from groups which include the subject patient, such as groups based on age and sex, in order to measure neural degeneration or regeneration.

Therefore, in one aspect, the invention comprises a method of diagnosis of or monitoring the progression or regression of a neurological impairment in a patient, comprising the steps of: (a) presenting a first sensory stimulus to the patient; (b) presenting a second sensory stimulus to the patient; (c) wherein the first sensory stimulus and second sensory stimulus are temporally separated by a period of time (SOA); (d) determining the patient's perception of the two stimuli as either simultaneous or sequential for that particular SOA; (e) repeating steps (a) through (d) with different SOA's until the simultaneity threshold SOA is determined; and (f) comparing the simultaneity threshold SOA to baseline or control data.

The sensory stimuli may be visual, tactile or auditory. In a preferred embodiment, both visual and tactile testing is implemented. The stimuli may be presented bilaterally or unilaterally. In one embodiment, the visual stimuli are red LEDs and the tactile stimuli are punctate stimuli with a blunt pin or rod. The tactile stimuli may be presented to any body part. In one embodiment, the tactile stimuli are delivered to the patient's fingertips.

Interhemispheric transfer times may be estimated and compared with baseline or control data. IHTTs may be estimated by determining the difference between bilateral and unilateral simultaneity thresholds.

In another aspect, the invention may comprise an apparatus for diagnosing a neurological impairment in a patient, comprising:(a)computer-implemented control means for delivering pairs of sensory stimuli to the patient, including a timing control means, wherein each pair comprises first and second sensory stimuli temporally separated by an SOA;(b)an array of visual stimuli operably connected to the control means; and(c)an array of tactile stimulators operably connected to the control means.

BRIEF DESCRIPTION OF THE DRAWINGS

The invention will now be described by way of an exemplary embodiment with reference to the accompanying simplified, diagrammatic, not-to-scale drawings. In the drawings.

DETAILED DESCRIPTION

When describing the present invention, the following terms have the following meanings, unless indicated otherwise. All terms not defined herein have their common art-recognized meanings. The term "neurological impairment" refers to a disease or condition which is caused by or is characterized by a degeneration in nerve conduction. Examples of neurological impairments, as used herein, include without limitation multiple sclerosis, Parkinson's Disease, head trauma, Alzheimer's Disease, and sequelae from a stroke.

Figure 1:
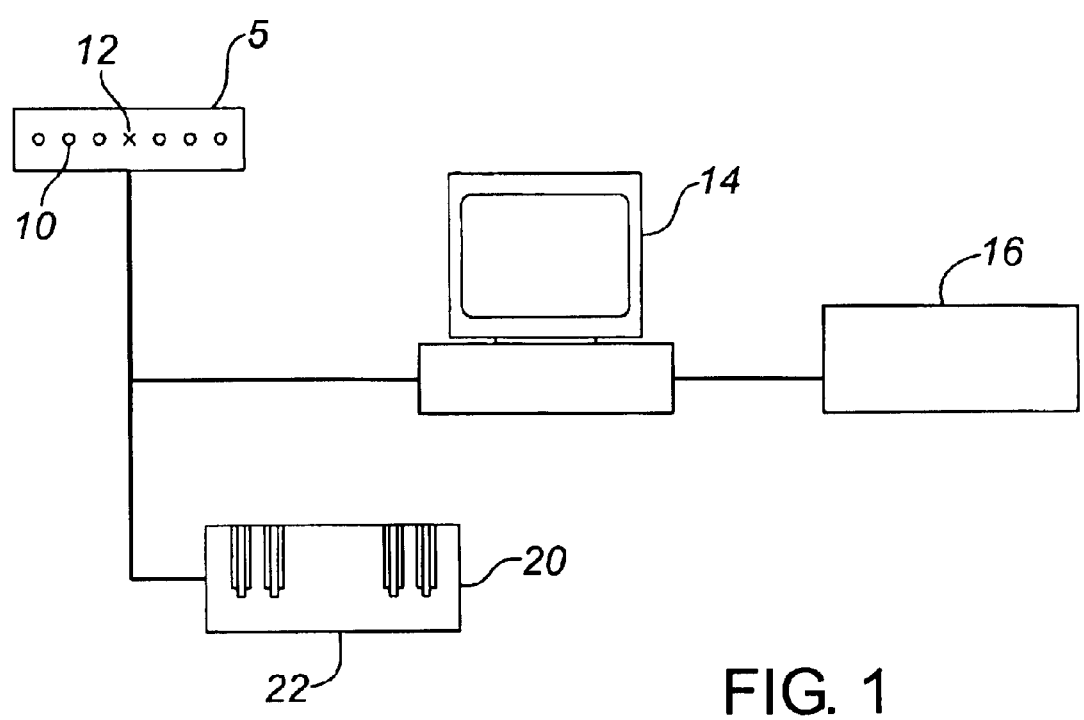
FIG. 1 shows a schematic representation of a combined visual/tactile testing system of the present invention.
Figure 2:
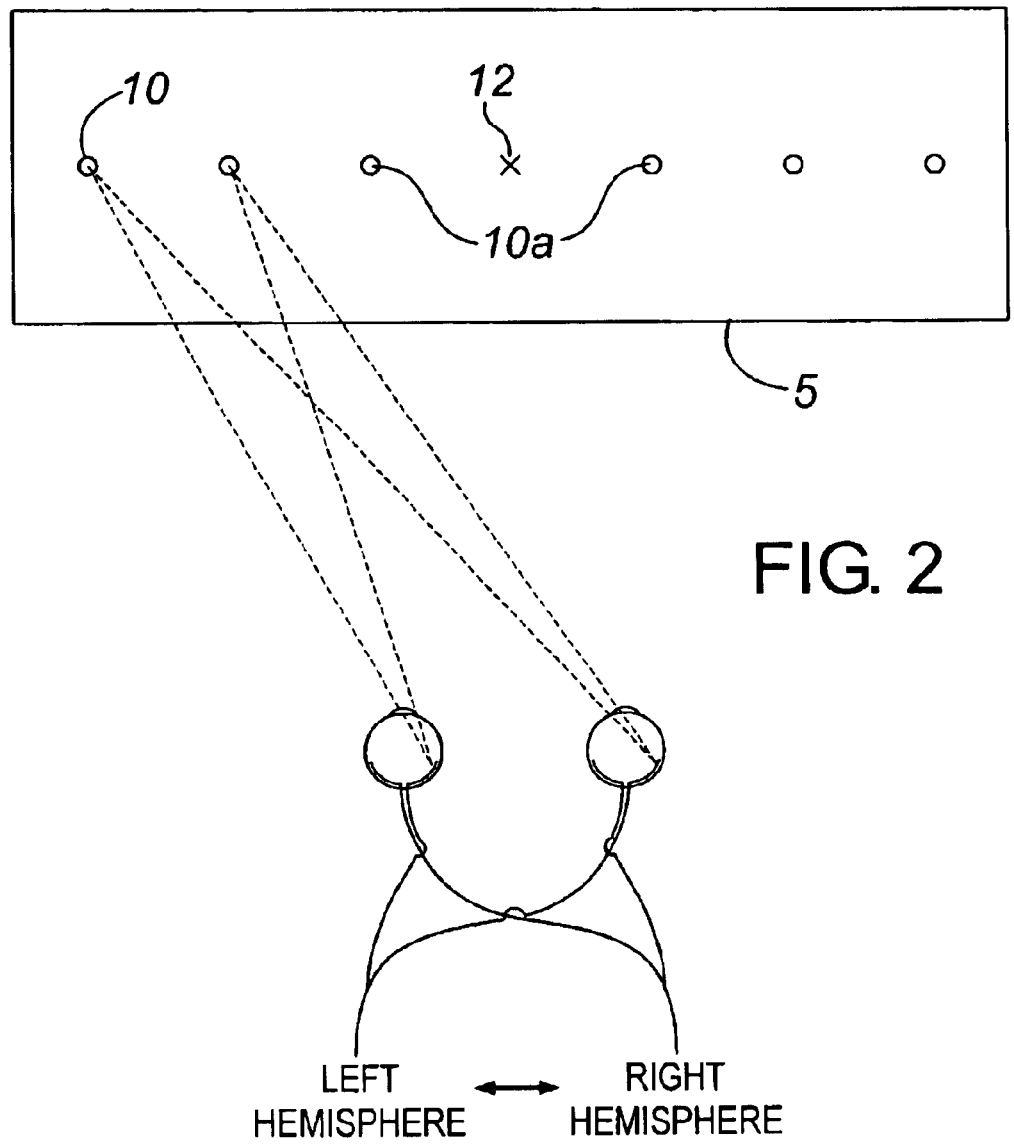
FIG. 2 shows a schematic representation of a visual testing system of the present invention, where a unilateral presentation of LEDs is shown.

In general terms, and with reference to FIG. 1, the invention comprises a combined visual and tactile test apparatus designed to measure a patient's simultaneity thresholds between two sensory stimuli such as visual stimuli or tactile stimuli. The time interval (stimulus onset asynchrony or SOA) between the onset of the first stimulus to the onset of the second stimulus is adjusted until the threshold SOA is determined. A simultaneity threshold is the longest duration of time between onset of a first stimulus and the onset of a second stimulus which is perceived by the patient to be simultaneous onsets and not sequential onsets.

In one embodiment, perceived simultaneity of visual stimuli is tested with an apparatus (5) comprising of at least one pair of red light emitting diodes (LEDs) (10) and a head/chin rest (not shown) which immobilizes the patient in position to view the LEDs (10). Other suitable visual stimuli may be known to those skilled in the art. A black cross (12) or other mark is centred between the pair of LEDs (10) which serves as a central fixation point for the patient. In an alternative embodiment, multiple pairs of LEDs may be used, preferably in a horizontal plane as shown in FIG. 1. In the embodiment shown, the inner pair (10a) of LEDs are spaced from the fixation point by 3.3° of visual angle. Each LED is preferably separated from adjacent LEDs by at least 3.0° of visual angle. At a viewing distance of 57 cm, one cm of lateral distance subtends to one degree of visual angle.

The LEDs may be placed in various positions in the patient's visual field. Different results from different placements may provide localization information to the practitioner. For example, with the LED configuration shown in FIG. 1, if statistically different results are obtained using the two far right LEDs in a unilateral test, as opposed to the inner pair of right LEDs in a unilateral test, that result may provide clinically significant information to the practitioner. Similarly, if a left field unilateral test is significantly different from a right field unilateral test, that result may be clinically significant. The different combinations of testing will be apparent to one skilled in the art.

In one embodiment, the LEDs emit a red light of an intensity of about 123 cd/m$^2$ against a light background having a luminance of about 46 cd/m$^2$. The illumination and contrast must be sufficient that visual ability or acuity is not a factor when testing.

The LEDs are activated by a control program running on a computer (14) which includes or is connected to an accurate timing mechanism capable of delivering a consistent timing signal in the millisecond range. In one embodiment, a timing control box (16) uses a crystal controlled oscillator which runs at 4.096 MHz to deliver the stimuli in a precise manner. The oscillator signal is divided by 4096 to provide a very accurate and highly stable 1 ms output signal which is used by the control program to deliver the stimuli with precise timing.

The control program allows the practitioner to choose the two LEDs to be illuminated and the SOA between the illumination of the first LED and the second LED. The LEDs may be illuminated in a bilateral fashion where a LED in the left visual field which projects to the right hemisphere and a LED in the right visual field which projects to the left hemisphere are illuminated in pairs. Alternatively, the LEDs may be illuminated in a unilateral manner, where both LEDs are illuminated in succession in one of the left or right visual fields.

Figure 3:
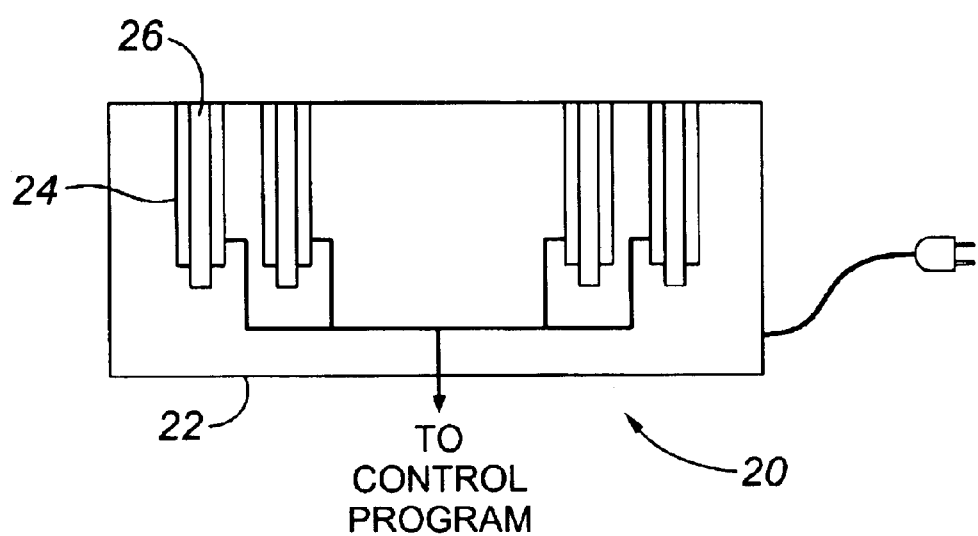
FIG. 3 shows a tactile stimulator used for tactile testing in one embodiment of the present invention.

The control program may control the tactile stimulators in like fashion. As shown in FIGS. 1 and 3, in one embodiment, the tactile stimulators (20) comprise four solenoid activated pins, grouped in pairs, for delivering a punctate stimulation to the patient's fingertips. A box (22) which houses the four pins may include a hand/wrist rest (not shown) which positions the fingertips over the openings through which the pins are activated. One embodiment of the tactile stimulus delivery apparatus is illustrated in FIG. 3. When the solenoids (24) are charged, the pin (26) or rod is thrust upwards through the core of the solenoid and delivers a punctate stimulation to the palmar surface of the fingertip that is resting on the holder. In one embodiment, the duration or hang time of the rod can be as short as 10 ms with 1 mm vertical extension above the housing (skin depression). These values may be programmed into the control program and may be varied as desired. For comparison purposes, it is desirable to have the same settings for the two stimulators.

It is preferable to isolate the limbs being tested as well as mask aural cues of the solenoids so that the patient may only rely on the tactile sensation in making the requested judgements. For example, if the fingertips are being tested, it is preferred to rest the patient's forearms against foam padding to minimize any vibrations that may result from the stimulus delivery. The patients may be fitted with earplugs and headphones which provide sound-proofing in order to mask the noise of the firing of the solenoids. In addition, if necessary, the headphones may deliver pink noise to mask any aural cues of the solenoids.

The computer controller may be programmed with an algorithm in order to control the delivery of the visual or tactile stimuli. Any method of determining a psychophysical threshold may be used such as ascending or descending SOAs where the SOA is set well above or well below the threshold level and is increased or decreased until the threshold is passed. In a preferred embodiment, a version of the well-known Parameter Estimation by Sequential Testing (PEST) algorithm is well suited for this application, as it permits the determination of the simultaneity threshold in as few trials as possible. Suitable PEST algorithms are described in Findlay J. M. (1978); Estimates on probability functions: a more virulent PEST. *Perception and Psychophysics*, 23, 181; and in Pentland, A. (1980) Maximum likelihood estimation: The best PEST. *Perception and Psychophysics*, 28, 377; the contents of which are incorporated herein by reference. The testing values of the PEST technique are determined by a set of rules which operate by using a binary forced-choice (YES/NO) paradigm. The time interval or SOA between the onset of the first stimulus to the onset of the second stimulus was adjusted, either increased or decreased according to the patient's previous response. PEST algorithms are characterized by large step sizes at the beginning of testing, which step sizes reduce as the test value gets closer to the threshold value. In one embodiment, the SOA step size changed by a constant value in association with NO responses, and the SOA step size would increase by half the previous SOA value in association with YES responses. Thus, a value change in SOA step sizes only occurred with step reversals associated with YES responses. The program would terminate when the SOA step size reached 1 ms.

Where there are three LEDs in each visual field, on either side of the central fixation point, many different bilateral and unilateral pairings may be used. In one embodiment, the outer LEDs may be used in one bilateral pairing, the middle LEDs used in another bilateral pairing and the inner LEDs in yet another pairing. Unilateral pairings will be apparent. In each pairing, one LED will be illuminated before the other, and then both will remain illuminated for the same length of time after the second LED is illuminated; ensuring that both LEDs go dark at the same time. The initial SOA step size may be set at 10 ms and the termination step size SOA may be set at 1 ms. The timing mechanism of the present invention preferably permit accurate timing down to the 1 ms level. The simultaneity threshold was that SOA value which terminated the PEST program.

In visual testing, a patient is instructed to focus on the central fixation point with their chin resting on the chin rest. The patient may be instructed that there are no right or wrong answers and they are simply to use their best judgement. After each delivery of a stimulus pair, the patient is asked to respond YES if they judged the illumination onsets to be simultaneous and NO if they judged the illumination onsets to be staggered. Verbal responses are then recorded by the tester, after each answer, the tester may then trigger the next stimulus pair. The PEST algorithm terminates when the SOA step size reaches its smallest value. The simultaneity threshold is the highest value of the SOA where the patient still perceives simultaneous stimuli.

We have found that average simultaneity thresholds support the hemispheric equivalence model as proposed by Geffen et al. (1996). Typically, there are no significant threshold differences in stimulus order (left before right, or right before left) in bilateral testing. Unilateral testing in the different visual fields also do not indicate a hemispheric advantage. Bilateral simultaneity thresholds versus unilateral thresholds testing were significantly greater, suggesting that interhemispheric transfer was required for simultaneity judgements.

We have found that the ability to make simultaneity judgements becomes impaired with advancing age. Overall mean visual simultaneity thresholds increased with age among healthy adults. The threshold for young adults (18 to 39 years of age) was 28.33 ms (SD=10.97), for middle aged adults (40 to 55 years of age) the threshold was 38.56 ms (SD=17.46), and for older adults (60 to 80 years of age) the threshold observed was 65.84 ms (SD=22.69).

A significant deterioration is observable in patients known to have MS. Average visual simultaneity thresholds for MS patients was 63.82 ms (SD=21.35), as compared to 38.56 ms (SD=17.46) recorded for age-and-gender matched controls (baseline, normalized data). Therefore, if a patient who is suspected of having MS demonstrated simultaneity thresholds significantly higher than the average thresholds for individuals of similar age and gender, that is a diagnostic indicator that the patient does indeed have MS. It of course is not a sole and conclusive diagnostic test, but can be diagnostic in combination with other known tests and observations. Once threshold data for an individual suffering from a neurological impairment such as MS is determined, continued periodic testing may monitor the progression or regression of the impairment in the normal course or in response to some therapy.

Visual interhemispheric transfer times (IHTTs) are calculated by subtracting the mean thresholds of the two inner unilateral conditions (the two inner LEDs on each side of the center mark) from the mean threshold of the bilateral condition (the inner pair of LEDs). Interhemispheric transfer times increased significantly for both older adults and for MS patients. Data for IHTTs are as follows: 5.64 ms (SD=6.99) for older adults; 3.21 ms (SD=5.18) for younger adults; 9.61 ms (SD=7.60) for MS patients compared with 3.15 (SD=5.10) for gender-and-age matched controls. These results support the hypothesis that MS induced damage to the corpus callosum slows central nerve conduction considerably. All of the above findings were statistically significant.

In addition to visual simultaneity temporal testing, tactile testing may be used alternately or in conjunction with the visual testing. The same PEST algorithm may be employed, however, the computer control program is used to actuate solenoid activated blunt pins which stimulate a body part of the patient, rather than LED visual stimuli. Similar to the visual testing, pairs of innocuous stimuli such as blunt pins or mild electric shocks are delivered to the patient's body. Other tactile stimuli and stimulators may be known to those skilled in the art. The patient's ability to time the onset of the tactile stimuli may be tested in a bilateral situation where each of the pair of stimuli is delivered to both sides of the body or in unilateral situations where both stimuli of the pair is delivered to one side of the body. In one embodiment, where pins are used to stimulate the fingertips of the patient, the patient rests the index and middle fingers (same bundle of nerve fibers) of both hands in an interwoven manner on holders that are located above the pins. When activated, the stimulator delivers a punctate stimulation to a pair of fingertips. Bilateral stimulation involves both index fingers on both hands, while unilateral stimulation involves the index and middle fingers of each of the left and right hand. Bilateral stimulation to the body involves interhemispheric transfer since the somatosensory system is a crossed modality. Tactile interhemispheric transfer times (IHTTs) are calculated by subtracting the mean threshold of the two unilateral conditions (index and middle finger stimulation of either left or right hand) from the bilateral condition (index or middle finger stimulation of both hands).

The same PEST algorithm described above in connection with visual testing may be used to determine the simultaneity threshold. The simultaneity threshold may vary according to the body part being stimulated. For example, longer nerve pathways (e.g., leg stimulation) will result in higher thresholds relative to shorter pathways (e.g., arm). However, if the simultaneity threshold is much higher, it may indicate that peripheral nerve conduction in that part of the body is impaired. Likewise, significantly different simultaneity threshold values for the left-and-right side of the body may indicate a differential decline in neural processing.

With tactile testing, we have again found that significant age related differences exist: Simultaneity thresholds of young adults (18 to 39 years of age) averaged about 26 ms (SD=9.85) while those of older adults (60 to 80 years of age) averaged about 61 ms (SD=16.03). In a population of patients known to have MS, the simultaneity thresholds averaged 56 ms (SD=19.82), compared with 33 ms (SD=13.04) for age and gender matched controls.

Measurement of central conduction (IHTT) demonstrated similar differences. IHTTs in older adults averaged 20.33 ms (SD=15.36) while IHTTs in younger adults averaged 9.23 ms (SD=6.71). MS patients demonstrated IHTTs averaging 22.7 ms (SD=10.10), compared to 8.73 ms (SD=3.17) for age-and gender matched controls. Given the pathways of the corpus callosum, interhemispheric transfer is typically longer for somatosensory information relative to visual information. The reported findings above were all statistically significant.

It is notable that simultaneity thresholds for both visual and tactile tests nearly doubled for MS patients compared to a control population, whereas IHTTs showed an increase of about 2.6× in MS patients. These results demonstrate that measurement of both simultaneity thresholds and of IHTTs may be reliable diagnostic indicators.

In one preferred embodiment, tactile testing is alternated with visual testing and bilateral testing is alternated with unilateral testing. As is apparent, four different tests may be conducted in a test procedure: bilateral visual, unilateral visual, bilateral tactile, and unilateral tactile. For example, a first round of testing may involve a bilateral visual test, followed by bilateral tactile testing using the patient's index fingers, followed by right visual field unilateral test, followed by tactile testing using the patient's torso. The course and sequence of testing may continue as the tester may desire until a sufficiency of statistically significant data is obtained.

As will be apparent to those skilled in the art, various modifications, adaptations and variations of the foregoing specific disclosure can be made without departing from the scope of the invention claimed herein.

What is claimed is:

1. A method of diagnosis of or monitoring the progression or regression of a neurological impairment in a patient, comprising the steps of:
   (a) presenting a first sensory stimulus to the patient;
   (b) presenting a second sensory stimulus to the patient;
   (c) wherein the first sensory stimulus and second sensory stimulus are temporally separated by a period of time (SOA);
   (d) determining the patient's perception of the two stimuli as either simutaneous or sequential for that particular SOA;
   (e) repeating steps (a) through (d) with different SOA's until a simultaneity threshold SOA is determined; and
   (f) comparing the simultaneity threshold SOA to baseline or control data.

2. The method of claim 1 wherein the first and second sensory stimuli are visual stimuli.

3. The method of claim 2 wherein the first and second visual stimuli are presented bilaterally to the patient.

4. The method of claim 2 wherein the first and second visual stimuli are presented unilaterally to the patient.

5. The method of claim 2 wherein each of the visual stimuli is the illumination of a LED.

6. The method of claim 5 wherein each of the LEDs are separated by at least 3.0° in the patient's visual field.

7. The method of claim 1 further comprising the step of determining the patient's interhemispheric transfer time (IHTT) by determining the patient's simultaneity threshold SOA for a bilateral presentation of the stimuli and subtracting the patient's simultaneity threshold SOA for a unilateral presentation of the stimuli; and comparing the IHTT to baseline or control data.

8. The method of claim 1 wherein the first and second sensory stimuli are tactile stimuli.

9. The method of claim 8 wherein the first and second tactile stimuli are presented unilaterally.

10. The method of claim 8 wherein the first and second tactile stimuli are presented bilaterally.

11. The method of claim 8 wherein each of the tactile stimuli is mechanical stimulation by a rod.

12. The method of claim 1 wherein steps (a) through (f) are performed with visual stimuli and then repeated with tactile stimuli.

13. The method of claim 12 further comprising the step of determining a IHTT for one or both of visual and tactile stimuli and comparing the IHTT to baseline or control data.

14. The method of claim 1 wherein the simultaneity threshold SOA is determined in accordance with a parameter estimation by sequential testing algorithm.

15. An apparatus for diagnosing a neurological impairment in a patient, comprising:

(a) computer-implemented control means for delivering pairs of sensory stimuli to the patient, including a timing control means, wherein each pair comprises first and second sensory stimuli temporally separated by a period of time (SOA);

(b) an array of visual stimuli operably connected to the computer-implemented control means; and (c) an array of tactile stimulators operably connected to the computer-implemented control means.

16. The apparatus of claim 15 wherein the timing control means comprises a crystal controlled oscillator.

17. The apparatus of claim 15 wherein the visual stimuli comprise LEDs.

18. The apparatus of claim 15 wherein the tactile stimulators comprise electromechanically actuated pins.

* * * * *